US006485623B1

(12) United States Patent
Anderson (10) Patent No.: US 6,485,623 B1
(45) Date of Patent: Nov. 26, 2002

(54) METHOD AND DEVICE FOR FORMING ANGLED WELLS IN AN ELECTROPHORESIS GEL SLAB

(75) Inventor: N. Leigh Anderson, Washington, DC (US)

(73) Assignee: Large Scale Proteomics Corp., Germantown, MD (US)

( * ) Notice: Subject to any disclaimer, the term of this patent is extended or adjusted under 35 U.S.C. 154(b) by 45 days.

(21) Appl. No.: 09/721,710

(22) Filed: Nov. 27, 2000

(51) Int. Cl.$^7$ .................. G01N 27/453; A45D 24/00; B29C 39/00; B29C 39/02
(52) U.S. Cl. .................. 204/466; 204/467; 204/616; 204/618; 204/620; 249/64; 249/176; 264/299; 264/334; 132/160
(58) Field of Search .................. 204/466, 467, 204/456, 606, 616, 618, 619, 620; 249/64, 176; 264/299, 334; 132/160

(56) References Cited

U.S. PATENT DOCUMENTS

| D68,282 S | * | 9/1925 | Van Ecker .................. D28/21 |
| 1,819,433 A | * | 8/1931 | Miller .................. 132/139 |
| 3,205,903 A | * | 9/1965 | D'avanzo .................. 132/139 |
| D206,527 S | * | 12/1966 | Montecalvo .................. D30/159 |
| 5,073,246 A | | 12/1991 | Chu et al. .................. 204/619 |
| 5,164,065 A | | 11/1992 | Bettencourt et al. .................. 204/619 |
| 5,284,565 A | | 2/1994 | Chu et al. .................. 204/619 |
| 5,993,628 A | | 11/1999 | Selby et al. .................. 204/470 |

OTHER PUBLICATIONS

Derwent abstract of M. L. Schaarschmidt (ZA–9609277–A).*

* cited by examiner

Primary Examiner—Jill Warden
Assistant Examiner—Alex Noguerola
(74) Attorney, Agent, or Firm—Roylance, Abrams, Berdo & Goodman, L.L.P.

(57) ABSTRACT

A device for forming angled wells in an electrophoresis gel slab includes a device having a plurality of projections oriented at an angle with respect to a longitudinal dimension of the device. A method for forming angled wells in a gel places the device in a gel forming material and allows the material to polymerize to form the electrophoresis gel slab. The device can be removed from the gel slab without distorting or tearing the gel and forming a plurality of substantially uniform sample wells oriented at an angle with respect to the edge of the gel slab. The sample wells are dimensioned to contain a liquid sample for electrophoresis separation. The gel slab can be rotated 90° so that the sample wells are oriented along a vertical edge of the gel slab with the sample wells retaining the liquid sample therein.

52 Claims, 6 Drawing Sheets

METHOD AND DEVICE FOR FORMING ANGLED WELLS IN AN ELECTROPHORESIS GEL SLAB

FIELD OF THE INVENTION

The present invention is directed to a method and device for forming sample wells in an electrophoresis gel slab. More particularly, the invention is directed to a method and device for forming a plurality of angled sample wells along a vertical edge of a gel slab for retaining liquid samples during a first dimension electrophoresis.

BACKGROUND OF THE INVENTION

The separation of proteins and other macromolecules is often carried out by a slab gel electrophoresis separation in which the sample migrates through the gel slab, to a point determined by the molecular weight of the molecules in the sample. The gel acts as a sieve to separate the molecules according to their molecular weight.

This separation is often performed by a sodium dodecyl sulfate electrophoresis process within a two-dimensional acrylamide gel slab. A gel-forming composition is placed between two glass plates. The glass plates include spacers at opposite side edges to form a uniform gap between the plates. A seal may be placed along the open bottom edge, and the gap is filled with the gel-forming composition or the plates filled while in an enclosing box. The gel forming composition is allowed to set and the sample is placed along the edge of the gel slab. The protein sample may be a spaghetti-like strip of an isoelectric focusing gel that has been removed from a gel tube after a first dimension electrophoresis process. Alternatively, a liquid sample can be placed in a well that is formed in the end of the gel slab.

The open ends of the gel slab are placed in contact with buffer solutions and an electric potential is applied between the ends of the gel slab to cause the molecules to migrate through the gel slab. The gel slabs can be oriented vertically so that the molecules migrate downward through the gel slab.

A suitable apparatus for electrophoresis separation on a gel slab is disclosed in U.S. Pat. No. 4,088,561 to Anderson which is hereby incorporated by reference in its entirety. This apparatus contains a tank for supporting a plurality of slab gels supported between glass plates. Non-liquid samples are placed along the side edge of the gel slab so that the molecules migrate from one side edge to the opposite side edge in a horizontal direction. Seals are provided in the tank along the opposite side edges of the glass plates to contain and isolate the respective buffer solution at each end of the gel slab. Electrodes are provided at opposite ends to apply the electric potential between the open ends of the gel slab.

Slab gels are also used for separation of liquid samples that have been prepared by various techniques. Liquid samples are often prepared by centrifuging the protein sample to isolate certain cell fractions based on the separation of layers by the centrifuge or by solubilization of whole tissues or body fluids. Indentations or wells are formed along the edge of the gel slab to receive the liquid sample during the electrophoresis separation. Typically, the sample wells are formed in the end of the gel slab or in the end of an attached stacking gel by inserting a notched device into the end of the gel forming material and allowing the gel to set around the notches. The notches are typically square teeth that are inserted straight into the gel perpendicular to the edge of the gel slab. The device is then removed from the gel to provide the sample wells.

One example of a device, referred to as a comb, for forming wells in a gel slab is disclosed in U.S. Pat. No. 5,164,065 to Bettencourt et al. The comb includes a plurality of sharp teeth extending from a plate. The teeth are inserted into the bottom edge of a gel for forming lanes for separating the samples. The comb is removed from the gel and placed along the top edge of the gel. The spaces between the teeth receive the samples for separation.

The electrophoresis gels are fragile and can stick to the comb or well-forming device as the gel sets. It is often difficult to remove the gel-forming device without damaging or tearing portions of the gel slab. The suction effect caused by removing the teeth from the gel often causes the wells to collapse and distort. The result is a gel slab that has an inconsistent number of sample wells and sample wells that are different shapes and sizes due to the distortion and tearing of the gel. The wells are formed in the edge of the gel slab so that the gel slab cannot be rotated 90° without spilling the liquid sample.

In view of the deficiencies of the above-noted devices, there is a continuing need in the industry for an improved device for forming sample wells in an electrophoresis gel slab.

SUMMARY OF THE INVENTION

The present invention is directed to a method and device for forming sample wells in the edge of an electrophoresis gel slab. More particularly, the invention is directed to a method and device for forming angled sample wells along a vertical edge of the gel slab for retaining liquid samples in a slab gel electrophoresis separation in which the gel is placed in an orientation such that the electrophoretic movement occurs in a horizontal direction.

Accordingly, a primary object of the invention is to provide a method and device for forming a plurality of spaced-apart sample wells along the vertical edge of a gel slab for containing a plurality of liquid samples.

Another object of the invention is to provide a method and device for forming sample wells along the edge of a gel slab substantially without distorting or tearing the gel material.

Still another object of the invention is to provide a method and device for forming sample wells in gel slabs for use in a DALT electrophoresis system.

A further object of the invention is to provide a sample well-forming device that can be removed from an electrophoresis gel-forming material after the gel has set without tearing the gel or collapsing the sample wells formed in the gel.

Another object of the invention is to provide a method and device for forming sample wells along the side edge of a gel slab for use in an automated second dimension electrophoresis process where the sample wells are formed to contain a liquid sample.

A further object of the invention is to provide a device for forming sample wells in a gel slab where the device has a plurality of projections that have a rounded tip such that the projections can be removed from the gel material after the gel has polymerized without tearing or distorting the sample wells formed in the gel by the projections.

Still another object of the invention is to provide a device for forming angled sample wells in a gel slab, where the device has a plurality of angled teeth having sides that converge to a rounded tip.

Another object of the invention is to provide a device for forming sample wells in a gel slab where the device has a plurality of spaced-apart projections having an axial passage for allowing air into the sample well formed in a gel slab as the projections are removed from the gel slab, thereby preventing collapse of the sample well formed in the gel.

A further object of the invention is to provide a device for forming a plurality of sample wells along the edge of a gel slab where the device has a plurality of projections having an axial passage and a removable pin received in the axial passage of each of the projections that can be removed after the gel has polymerized and before the projections are removed from the gel.

The objects of the invention are basically attained by providing a device for forming a plurality of sample wells in an electrophoresis gel slab. The device comprises a body having a longitudinal edge with a longitudinal dimension, and a plurality of uniformly spaced-apart projections extending from the longitudinal edge of the body at an incline with respect to the longitudinal dimension. The projections are oriented in a row and extend substantially parallel to each other. The projections have a dimension to form a sample well in a side edge of an electrophoresis gel slab.

The objects of the invention are further attained by providing a device for forming angled sample wells along a vertical edge of a gel slab. The device comprises a body having a longitudinal dimension and a longitudinal side edge, and a plurality of projections integrally formed with the body and having a dimension for forming sample wells in a side edge of an electrophoresis gel slab. The projections extend from the longitudinal side edge at an angle of about 30° to about 50° with respect to the longitudinal dimension. The projections further have a tip and first and second side edges converging to the tip. The first and second side edges are oriented at an angle with respect to each other to enable the projections to be removed from an electrophoresis gel substantially without distortion of the gel.

The objects of the invention are further attained by providing a method of forming an electrophoresis gel slab having a plurality of liquid sample wells. The process comprises the steps of: providing a gel-forming substance between two spaced apart supporting plates having an open side edge and positioning a well-forming device for forming sample wells in the open side edge of the supporting plates and into the gel-forming substance. The device has a body with a longitudinal edge with a longitudinal dimension, and a plurality of uniformly spaced apart projections extending from the body at an incline with respect to the longitudinal dimension. The gel forming substance is solidified to form an electrophoresis gel slab which has a side edge. The well-forming device is removed from the glass plates to form an electrophoresis gel slab between the supporting plates. The gel slab has a plurality of sample wells along the edge of the gel slab. Each of the sample wells is formed at an angle with respect to a longitudinal dimension of the side edge of the gel slab for retaining a liquid sample when the side edge of the gel slab is oriented vertically.

The objects and advantages are also attained by providing a process for separating substances by second dimension electrophoresis. The process comprises the steps of: forming an electrophoresis gel slab having a first longitudinal edge and a plurality of spaced-apart sample wells formed in the gel. The wells have an axial dimension defining a depth. The axial dimension of the wells is oriented at an incline with respect to the longitudinal edge of the gel slab. The gel slab further has a second longitudinal edge. Test liquid samples are placed in each of the sample wells. The gel slab is positioned in a second dimension electrophoresis tank with the longitudinal edge of the gel slab oriented vertically and the sample wells are positioned in the gel slab at an incline with respect to the longitudinal edge to retain the liquid samples in the wells. First and second longitudinal edges of the gel slab are contacted with a buffer solution which is less dense than the liquid samples permitting them to remain in the bottoms of the wells in hydrostatic equilibrium and an electric potential is applied between the first and second longitudinal ends of the gel slab to cause molecules in the samples to migrate through the gel slab.

The objects, advantages and salient features of the invention will become apparent to one skilled in the art in view of the following detailed description of the invention in conjunction with the annexed drawings which form a part of this original disclosure.

BRIEF DESCRIPTION OF THE DRAWINGS

The following is a brief description of the drawings, in which.

DETAILED DESCRIPTION OF THE INVENTION

The present invention is directed to a method and device for forming angled sample wells in the edge of an electrophoresis gel slab. The method and device of the invention are particularly suitable for forming sample wells along a vertical edge of a gel slab in a manner to retain a dense liquid sample during a slab gel electrophoresis separation process.

Referring to the drawings, the device 10 for forming sample wells in a gel slab includes a body 12 and a plurality of projections 14 extending from a bottom edge 17 of body 12. As discussed hereinafter in greater detail, projections 14 have a shape to enable the projections to be removed from a polymerized electrophoresis gel substantially without distortion or collapsing of the walls of the sample well formed in the gel by the projections.

Body 12 has a width defined by opposite ends 13 sufficient to allow easy handling of the device. Preferably, body 12 has a longitudinal top edge 15 having a dimension corresponding substantially to the longitudinal dimension of the gel slab. In the embodiment illustrated, body 12 is a substantially planar member having flat side faces 16. A plurality of holes 18 are formed in body 12 to assist in handling device 10.

Figure 3:
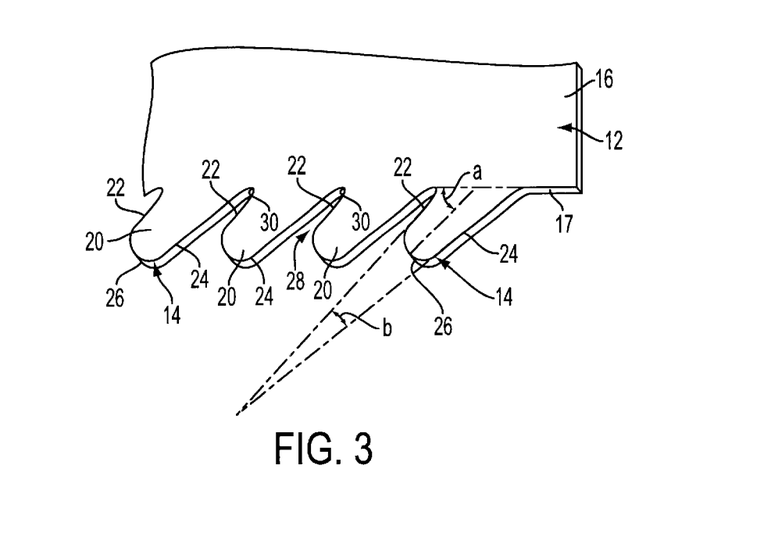
FIG. 3 is an enlarged sectional view of the device of FIG. 1 showing the details of the projections for forming the angled sampled wells.

In preferred embodiments, projections 14 extend from and are integrally formed with body 12 at an incline with respect to the longitudinal dimension of body 12. As shown in FIG. 3, projections 14 are oriented at an angle (a) of about 35° to about 50° with respect to the longitudinal dimension of body 12. In preferred embodiments, projections 14 are oriented at an angle of about 40–45° with respect to the longitudinal dimension of body 12. The actual angle of projections 14 can vary depending on the gel-forming material used to form the gel slab, the sample being analyzed and the volume of the sample being analyzed.

Projections 14 have a length and width to form a sample well of sufficient size to contain a volume of a liquid sample appropriate for slab gel electrophoresis. Preferably, projections 14 have a length of about 1 cm to about 1.5 cm measured from the tip of projections 14 to body 12.

In the embodiment of FIGS. 1–6, projections 14 are arranged in a row lying in the plane extending along a bottom edge 17 of body 12. Projections 14 have a thickness complementing the thickness of body 12 and include side faces 20 lying in the same plane as side faces 16 of body 12. Side faces 20 of projections 14 and side faces 16 of body 12 in a preferred embodiment are substantially flat. Preferably, projections 14 have a thickness substantially equal to or slightly less than the thickness of the gel slab.

Referring to FIG. 3, projections 14 are defined by a leading side edge 22 and a trailing side edge 24 extending between the side faces 20 of projections 14 and generally perpendicular to side faces 20. Side edges 22 and 24 are formed at an incline with respect to each other and converge toward a tip 26 of projection 14. Preferably, side edges 22 and 24 are substantially straight and terminate at rounded tip 26. In the embodiment illustrated, tip 26 has a substantially semicircular shape. Tip 26 typically has a radius of curvature of about 0.125 cm. Leading side edge 22 and trailing side edge 24 typically converge at an angle (b) of about 5° to about 15°, and preferably at an angle of about 10° with respect to each other, the respective projections 14 and bottom edge 17 of body 12. Projections 14 typically have a width of about 0.5 cm at the base of the respective projection 14 at bottom edge 17 of body 12. Projections 14 typically have a width of about 0.25 cm at tip 26.

Figure 1:
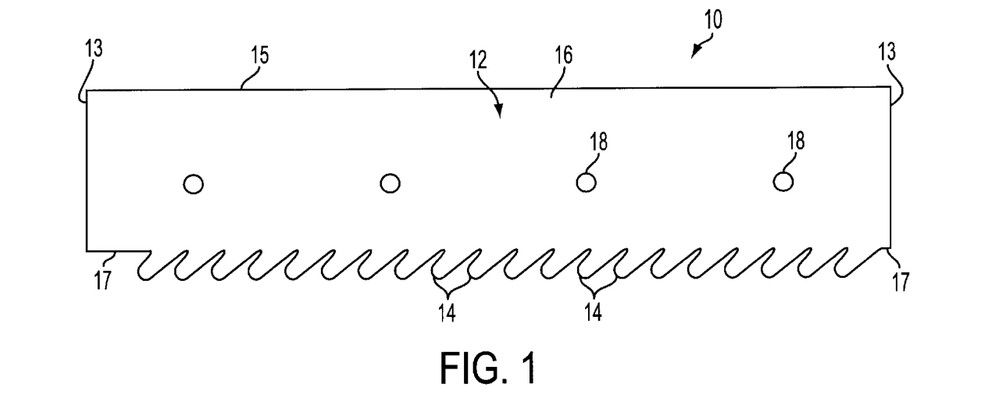
FIG. 1 is a side elevational view of the device for forming angled sample wells in a gel slab in a first embodiment of the invention.
Figure 2:
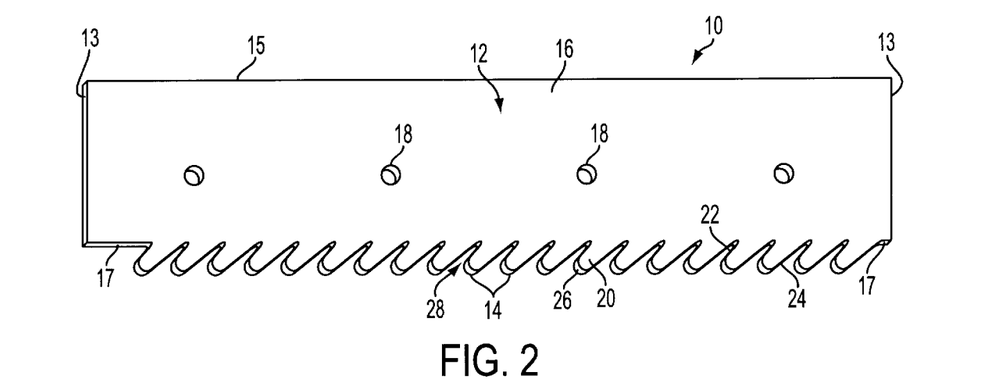
FIG. 2 is a perspective view of the device of FIG. 1.

As shown in FIGS. 1–3, projections 14 are spaced along body 12 to form a comb. Projections 14 are spaced apart a distance sufficient to enable each projection to form a sample well in the edge of an electrophoresis gel slab. Typically, projections 14 are spaced apart a distance of about ½ cm measured at the base between leading edge 22 and trailing edge 24 of adjacent projections 14. As shown in FIG. 3, adjacent projections 14 form a substantially V-shaped recess 28 with a semicircular bottom end 30.

Figure 4:
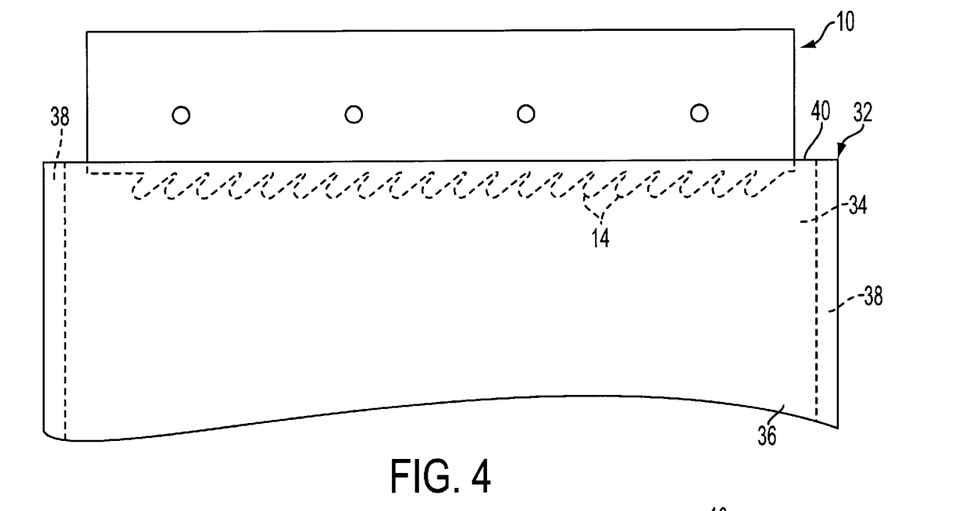
FIG. 4 is a side elevational view showing the device for forming the sample wells positioned in the edge of the gel-forming material prior to polymerizing.

Referring to FIG. 4, a gel slab 32 is prepared by forming a gel 34 between two glass plates 36 that are spaced apart by spacers 38. Spacers 38 are positioned along opposite ends of glass plates 36 and define the thickness of the gel 34 and the resulting gel slab 32. In a preferred embodiment, a gel forming material is placed between glass plates 36 with the open edge 40 of glass plates 36 facing upwardly. Device 10 is positioned in open edge 40 between glass plates 36 into the gel-forming material. The gel-forming material is then polymerized and allowed to set into gel 34. After the gel-forming material has set to form gel 34, device 10 is removed from gel 34. Preferably device 10 is pulled slowly from gel 34 in a linear direction with respect to the longitudinal dimension of projections 14. Gel 34 is a conventional gel used in a second dimension gel slab technology. Typically, the gel is an acrylamide SDS type gel as known in the art. In other embodiments, the gel may be a separating gel or a stacking gel above a separating gel.

Figure 5:
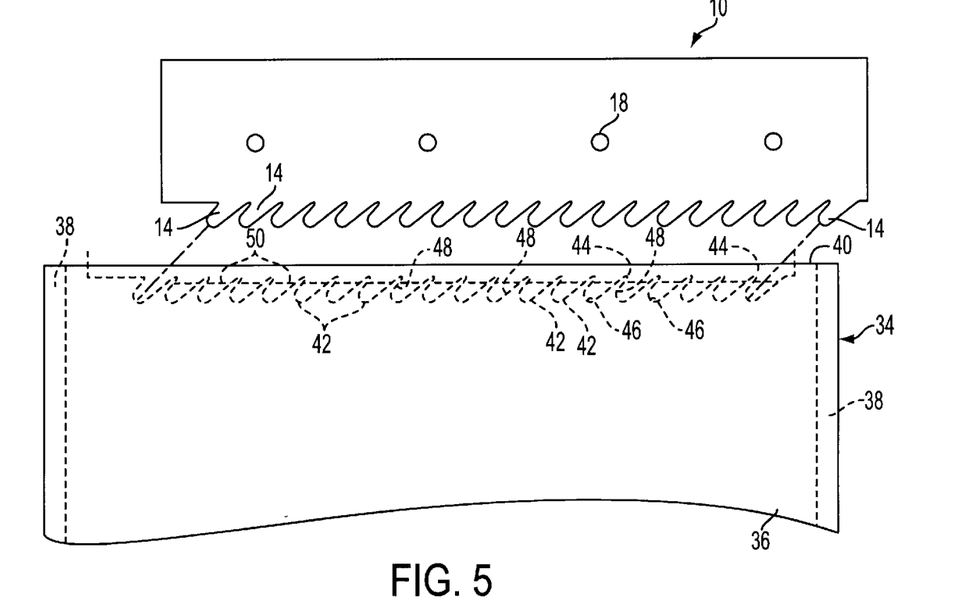
FIG. 5 is a side elevational view showing the device for forming the sample wells removed from the polymerized gel slab and showing the resulting sample wells containing a liquid where the gel slab is oriented in the horizontal position.

Leading side edge 22 and trailing side edge 24 of projections 14 are inclined at an angle with respect to each other to enable projections 14 to be separated from gel 34 and form a plurality of adjacent sample wells 42 where the sample wells 42 are separated by a wall 44. Recess 28 and bottom end 30 of recess 28 between adjacent projections 14 of device 10 are dimensioned to mold walls 44 in gel 34. Walls 44 have a sufficient width to provide wall 44 with adequate strength to resist being torn or separated from gel slab 34 when device 10 is removed from gel 34. As shown in FIG. 5, sample wells 42 having substantially uniform dimensions are spaced along the open edge of gel slab 34. Sample wells 42 in the embodiment illustrated are formed at an incline with respect to the plane of open end 40 of gel slab 32.

It has been found that the angle of convergence of leading edge 22 and trailing edge 24 of projections 14 and the curved tip 26 enable the projections 14 to release the wall 44 formed in gel 34 after polymerization. The incline of side edges 22 and 24 allow projections 14 to pull away from the gel, thereby allowing air to enter the sample well 42 to release the suction created when projections 14 are removed from the gel. Releasing the suction prevents sample wells 42 from collapsing and prevents wall 44 of sample walls 42 from tearing when projections 14 are pulled from the gel.

Sample wells 42 are formed with a concave bottom end 46 and inclined sides 48 that converge toward bottom end 46. Sample wells 42 are dimensioned to contain a sufficient volume of a liquid sample to be separated in a slab gel electrophoresis process. Liquid samples 50 are placed in each of the sample wells 42 as shown in FIG. 5. Liquid samples 50 can be placed in sample wells 42 manually or by automated robotic equipment for handling samples in protein analysis. Preferably, gel slab 32 is positioned with sample wells 42 facing upwardly as shown in FIG. 5 so that the liquid samples can be dispensed through a pipette or needle directly into a respective sample well 42. In alternative embodiments, gel slab 32 can be oriented at about a 45° angle such that sample wells 42 are oriented vertically with respect to a longitudinal axis of wells 42. This enables a pipette or needle to be inserted vertically into sample well 42 for dispensing the liquid sample directly on the bottom 46 of the respective well 42.

Figure 6:
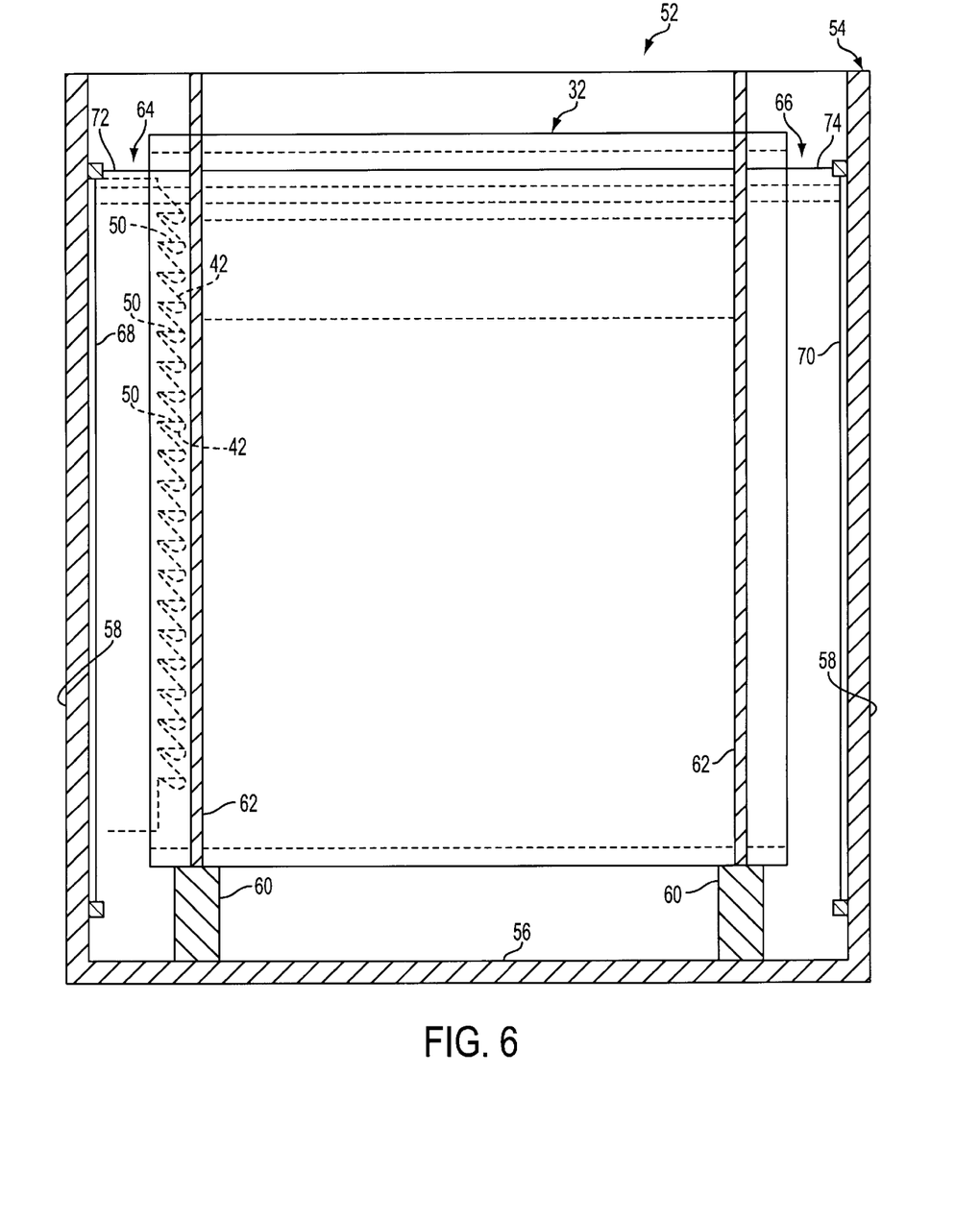
FIG. 6 is a side view in cross-section showing the gel slab positioned in the electrophoresis tank with the sample wells oriented along a vertical side edge of the gel slab and containing a liquid sample.

Gel slab 32 with sample wells 42 containing liquid sample 50 is rotated counterclockwise 90° to the position shown in FIG. 6 so that sample wells 42 open along a vertically-oriented edge of gel slab 32. Sample wells 42 are inclined with respect to the edge of gel slab 32 to retain the liquid sample within the respective sample well 42.

In the embodiment illustrated, device 10 is shown having twenty projections 14 extending from main body 12. In one embodiment of the invention, gel slab 32 is formed with as many as fifty sample wells 42, positioned along the longitudinal edge of the gel slab 32. Device 10 can be formed with a number of projections 14 corresponding to the desired number of sample wells in the gel slab. Alternatively, two or more identical devices 10 can be placed in an end-to-end relation in the open end of the gel slab to form the desired number of sample wells. Using several of the devices placed in series facilitates the removal of the device and the formation of uniform sample wells since the shorter devices can be easier to remove from the gel than a single device extending the entire length of the gel slab.

The samples 50 can be prepared by various processes commonly used in the industry for preparing samples for slab gel electrophoresis. The samples can be prepared, for example, by direct solubilization by 2-D centrifugation or organic solvent chromatography separation. In one embodiment, the liquid samples are prepared by a sedimentation rate separation followed by isopycnic separation. The resulting fraction can be mixed with a buffer solution in a small centrifuge tube to dilute the fraction. The tubes are centrifuged to pellet the subcellular particles. The supernatant is combined with a protein solubilizer, mixed with the particulate pellet, and stored in a 96 well plate. The samples are retrieved from the well plate and transferred to the sample wells 42 of the gel slab.

Referring to FIG. 6, gel slab 32 is placed in an electrophoresis separation apparatus 52. As a preferred embodiment, the electrophoresis separation apparatus is a DALT electrophoresis apparatus. Electrophoresis separation apparatus 52 includes a tank 54 having a bottom wall 56 and side walls 58. A support 60 is positioned along bottom wall 56 for supporting a plurality of gel slabs 32. Partitions (not shown) extend upwardly from support 60 to define slots for receiving gel slabs 32. A seal 62 extends from the edges of the partitions to contact the sides of gel slab 32 to form a relatively fluid tight seal and form a first chamber 64 around sample wells 42 and a second chamber 66 at the opposite open end of gel slab 32. A first electrode 68 is positioned in the first chamber 64 and a second electrode 70 is positioned in the second chamber 66. First and second chambers 64 and 66 are filled with a suitable buffer solution 72 and 74, respectively, as known in the art. An electric current is applied to electrodes 68 and 70 to form an electric potential between the ends of gel slab 32 causing the molecules of samples 50 to migrate through gel 34. A suitable electrophoresis apparatus is disclosed in U.S. Pat. No. 4,088,561 to Anderson, which is hereby incorporated by reference in its entirety.

It has been found that the angled wells formed in the gel slab can contain a sufficient volume of a liquid sample with the sample wells oriented along a vertical edge of the gel slab. The samples can be effectively subjected to electrophoresis separation. In the embodiment illustrated, sample wells 42 are open to the buffer solution in chamber 64. In preferred embodiments, sample wells 42 are closed after filling with the liquid sample to prevent excessive mixing of the buffer solution with the sample to reduce the possibility of the sample being washed from the sample well. The sample wells can be closed by applying a strip of the electrophoresis gel over the open end of the sample well. In further embodiments, a suitable tool can be used to press against the open end of the gel slab to deform the upper ends of the sample well sufficiently to close off the open end of the sample well.

Body 12 and projections 14 are preferably made of a suitable material that is non-reactive with the gel and can be separated from the gel slab after the gel has set. Typically, device 10 is formed from molded plastic, such as polyethylene, teflon, polyvinylchloride, methylmethacrylate, or polyester resins that can be separated easily from the gel.

In one embodiment of the invention, projections 14 include an outer layer or coating of an oxygen permeable material, such as polytetrafluoroethylene. The oxygen permeable layer allows oxygen to diffuse around the projections during the polymerization of the gel forming material. The oxygen generally inhibits the polymerization of the acrylamide gel forming material so that a thin layer of unpolymerized gel forming material remains around each of the projections. The unpolymerized material serves as a lubricant to enable the projections to be removed from the polymerized gel slab substantially without deforming or tearing the gel slab.

Referring to FIGS. 7–10, a second embodiment of the invention is illustrated. In this embodiment, a sample well forming device 80 includes a main body 82 having a plurality of projecting members 84 extending therefrom. As in the previous embodiment, projecting members 84 are arranged in a row and extend at an incline with respect to a longitudinal dimension of body 82. Preferably projecting members 84 extend from a bottom side 85 of main body 82 a substantially uniform distanced so that projecting members 84 form a uniform array. Typically projecting members 84 are inclined at an angle of about 40° with respect to main body 82.

Figure 7:
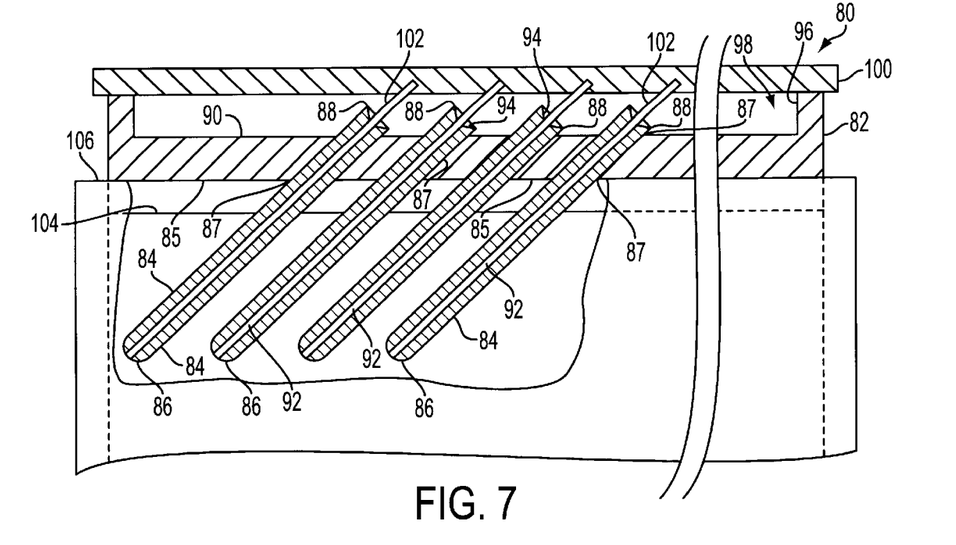
FIG. 7 is a side view in partial cross-section of a device for forming angled sample wells in a gel slab in a second embodiment of the invention.

Projecting members 84 have a generally cylindrical shape with a semispherical outer end 86. A top end 88 of projecting members 84 extend from a top face 90 of body 82. As shown in FIG. 7, projecting members 84 are discrete members that are inserted into angled apertures 87 in main body 82 and secured thereto by friction or by an adhesive or other bonding material. Each projecting member 84 can include an axial passage 92 extending from top end 88 to bottom end 86. Axial passage 92 at top end 88 includes a frustoconical shaped recess 94 with inclined surfaces converging toward outer end 86.

In the embodiment illustrated, body 82 includes upstanding end walls 96 to form a recessed area 98. Body 82 includes a removable top wall 100 having a plurality of pins 102 extending from a bottom surface thereof. Top wall 100 serves as a support plate for pins 102. Pins 102 are spaced apart in a row corresponding to the spacing and orientation of projecting members 84. Pins 102 extend from top wall 100 at an incline with respect to top wall 100 to extend through a respective axial passage 92 of each projecting member 84. Pins 102 have a diameter complementing axial passage 92 to effectively close axial passage 92. Pins 102 have an axial length complementing the length of projecting members 84. As shown in FIG. 7, pins 102 are coupled to top wall 100 and have a length to extend to outer end 86 of projecting member 84 when top wall 100 is positioned against end walls 96 of body 82.

Projecting members 84 have a diameter and a length sufficient to form a sample well in a gel slab as in the previous embodiment. Generally, projecting members 84 have a length sufficient to form a sample well having a length of about 1 cm to about 1.5 cm and a width of about 0.15 cm. Typically, the projecting members have a width substantially equal to the thickness of the gel slab and the spacing of the glass plates. As in the previous embodiment, projecting members 84 are inserted into the gel forming material of a gel slab 104 so that projecting members 84 are oriented at an incline with respect to the open end 106 of gel slab 104. The gel forming material is allowed to polymerize and set to form the gel slab.

Figure 8:
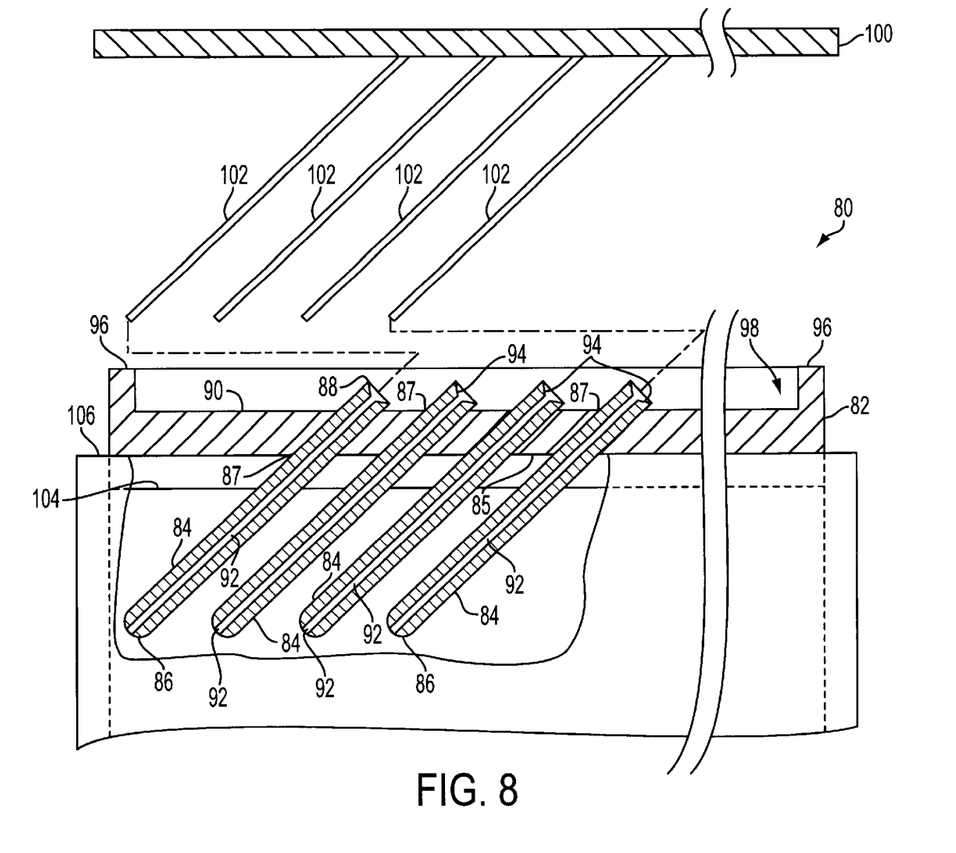
FIG. 8 is a side view in partial cross-section showing the pins removed from the axial passage of the projections in the device of FIG. 7.

After the gel-forming material polymerizes to form the gel slab, top wall 100 is lifted to retract pins 102 from the respective axial passage 92 of each projecting member 84 as shown in FIG. 8. Body 82 and projection members 84 can then be removed from the polymerized gel by pulling projecting members 84 from the gel in an axial direction with respect to a longitudinal axis of projecting members 84. Axial passage 92 in each of projecting members 84 allows air to enter the void as projecting members 84 are removed from the gel, thereby avoiding the formation of a vacuum and preventing the sample wells from collapsing.

Figure 9:
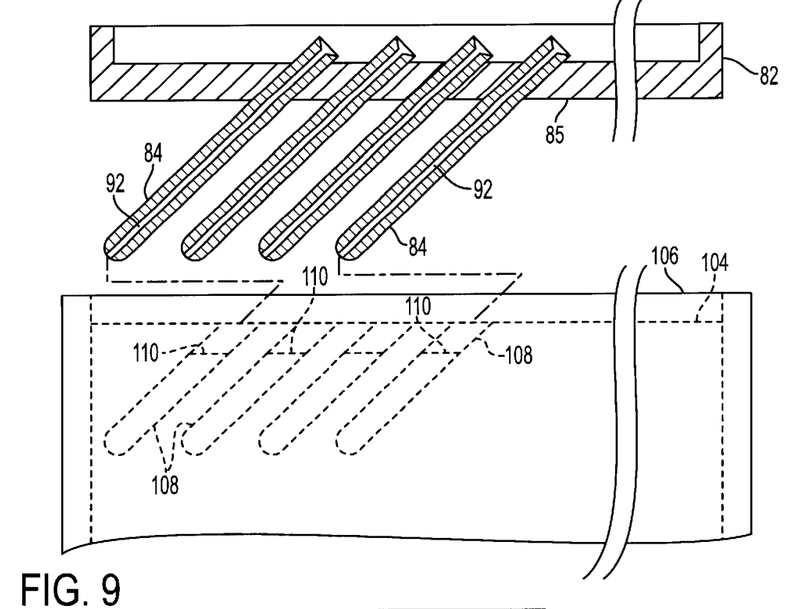
FIG. 9 is a side view in partial cross-section showing the device for forming the angled sample wells in the gel slab where the device is removed from the gel slab and the sample wells contain a liquid sample.
Figure 10:
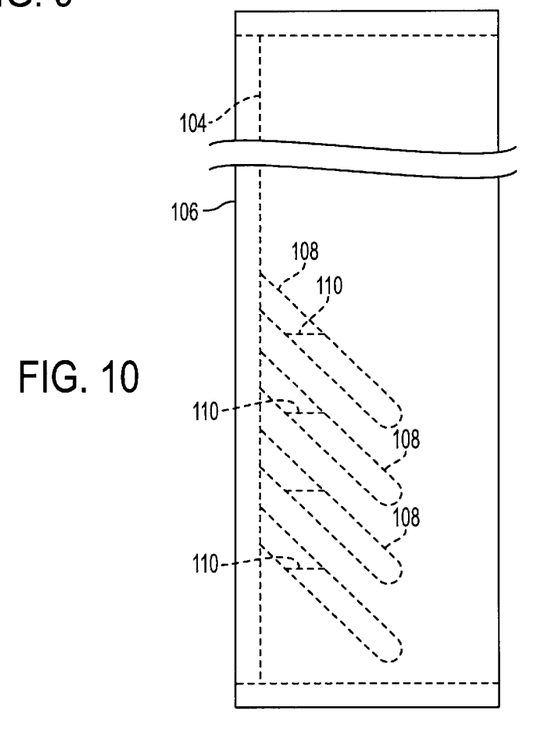
FIG. 10 is a side elevational view of the gel slab showing the sample wells in phantom lines oriented along a vertical side edge of the gel slab and containing a liquid sample for electrophoresis separation.

The resulting sample wells 108 as shown in FIG. 9, have a shape corresponding substantially to the shape of projecting members 84. A dense liquid sample 110 can then be placed in each sample well 108 as in the previous embodiments. Sample wells 108 are formed at a sufficient angle with respect to the edge of gel slab 104 to orient sample wells 108 along a vertical edge of gel slab 104 as shown in FIG. 10. The resulting gel slab with the samples 110 can then be subjected to the second dimension electrophoresis separation as in the previous embodiment.

In an alternative embodiment, projecting members 84 are solid members without the axial passages of the embodiment of FIGS. 7–10. The dimensions of the solid projecting members are preferably selected to reduce or minimize the collapsing and distortion of the wells formed in the gel slab.

Figure 11:
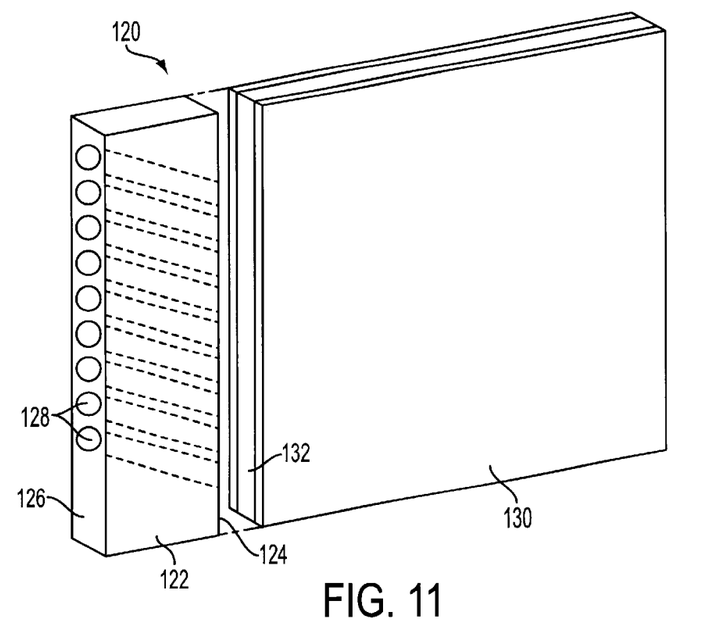
FIG. 11 is an exploded perspective view of the assembly in another embodiment of the invention.
Figure 12:
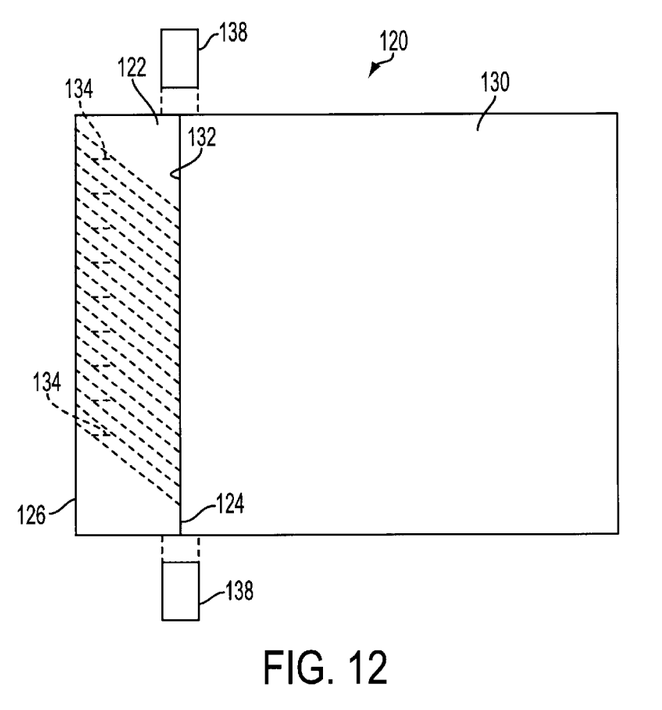
FIG. 12 is a front side elevational view of the assembly of FIG. 11.

Referring to FIGS. 11 and 12, a third embodiment of the invention is illustrated. In this embodiment, a sample well forming assembly 120 includes a body 122 having a substantially rectangular shape with a first longitudinal edge 124 and a second longitudinal edge 126. Body 122 has a longitudinal length corresponding substantially to the longitudinal edge of a gel slab.

Body 122 includes a plurality of channels 128 extending between first longitudinal edge 124 and second longitudinal edge 126. Channels 128 include a first open end at first longitudinal edge 124 and a second open end at second longitudinal edge 126. In preferred embodiments, channels 128 have a generally cylindrical shape with a longitudinal axis extending at an incline with respect to first longitudinal side edge 124. Channels 128 are parallel to each other and are dimensioned to hold an appropriate sample size for electrophoresis separation. Channels 128 typically are inclined at an angle of about 30° to about 50°, and preferably about 45° with respect to first longitudinal edge 124. The angle of channels 128 is sufficient to retain a suitable volume of a liquid sample.

Body 122 is coupled to a gel slab 130 along a longitudinal edge 132. Body 122 is positioned with first edge 124 contacting the electrophoresis gel to form a substantially fluid tight seal around the open end of each channel 128. Body 122 and gel slab 130 are oriented so that body 122 is vertical and forms a plurality of liquid sample wells along a vertical edge of gel slab 130. Body 122 can be coupled to gel slab 130 by an adhesive or suitable clamping device 138. A liquid sample 134 is placed in each channel 128 and the assembly is placed in an electrophoresis tank as in the previous embodiments.

While several embodiments have been chosen to illustrate the invention, it will be appreciated by those skilled in the art that various changes and modifications can be made without departing from the spirit and scope of the invention as defined in the appended claims.

What is claimed is:

1. A device for forming a plurality of sample wells in an electrophoresis gel slab, said device comprising:

a body having a longitudinal edge with a longitudinal dimension; and a plurality of spaced-apart projections extending from said longitudinal edge of said body at an incline with respect to said longitudinal dimension and in a plane of said body, said projections being oriented in a row and extending substantially parallel to each other, and said projections having a dimension to form a sample well in an edge of an electrophoresis gel slab, each of said projections having a first side edge extending from said longitudinal edge at a first angle and second side edge extending from said longitudinal edge at a second angle, said first side edge and said second side edge converging toward a substantially semicircular tip.

2. The device of claim 1, wherein each of said projections extends from said longitudinal edge at an angle of about 30° to about 50° with respect to said longitudinal dimension.

3. The device of claim 1, wherein each of said projections extends from said longitudinal side edge at an angle of about 40° with respect to said longitudinal dimension.

4. The device of claim 1, wherein each of said projections has a substantially planar configuration with substantially parallel first and second side faces.

5. The device of claim 1, wherein said first and second side edges converge at an angle of about 5° to about 15°.

6. The device of claim 1, wherein said first and second side edges converge at an angle of about 10°.

7. A device for forming a plurality of sample wells in an electrophoresis gel slab, said device comprising:

a body having a longitudinal edge with a longitudinal dimension; and a plurality of spaced-apart projections extending from said longitudinal edge of said body at an incline with respect to said longitudinal dimension, said projections being oriented in a row and extending substantially parallel to each other, and said projections having a dimension to form a sample well in an edge of an electrophoresis gel slab, wherein adjacent projections define a substantially V-shaped recess therebetween having a curved bottom end.

8. A device for forming a plurality of sample wells in an electrophoresis gel slab, said device comprising:

a body having a longitudinal edge with a longitudinal dimension; and a plurality of spaced-apart projections extending from said longitudinal edge of said body at an incline with respect to said longitudinal dimension, said projections being oriented in a row and extending substantially parallel to each other, and said projections having a dimension to form a sample well in an edge of an electrophoresis gel slab, wherein each of said projections has an axial passage extending therethrough and a removable pin received in said axial passage.

9. The device of claim 8, wherein said pin of each respective projection is coupled to a support member whereby said pins can be removed from said respective projections simultaneously.

10. The device of claim 8, wherein said projections have a substantially circular cross-section.

11. The device of claim 8, wherein said projections have a substantially spherical shaped tip.

12. The device of claim 8, wherein said projections extend from said body at an angle of about 40° from said longitudinal dimension.

13. A device for forming angled sample wells along a vertical edge of a gel slab, said device comprising:

a body having a longitudinal dimension and a longitudinal side edge; and a plurality of projections integrally formed with said body and having a dimension for forming sample wells in an edge of an electrophoresis gel slab, said projections extending from said longitudinal side edge, said projections further having a substantially semicircular tip and first and second side edges converging to said tip, said first and second side edges being oriented at an angle with respect to each other to enable said projections to be removed from an electrophoresis gel substantially without distortion of said gel, wherein said projections have first and second flat side faces oriented parallel to said longitudinal dimension of said body, and wherein said first and second side edges extend between said first and second faces.

14. The device of claim 13, wherein first and second side edges converge to said tip at an angle of about 5° to about 15°.

15. The device of claim 13, wherein said first and second side edges converge to said tip at an angle of about 10°.

16. The device of claim 13, Wherein said projections extend from said longitudinal side edge of said body at an incline of about 30° to about 50°.

17. A method of forming an electrophoresis gel slab having a plurality of liquid sample wells, said method comprising the steps of:

providing a gel-forming substance between two spaced apart supporting plates having an open side edge;

positioning a well-forming device for forming sample wells in said open side edge of said supporting plates and into said gel-forming substance, said device having a body with a longitudinal edge with a longitudinal dimension, and a plurality of uniformly spaced apart projections extending from said body at an incline with respect to said longitudinal dimension; and solidifying said gel forming substance to form an electrophoresis gel slab having a side edge, and removing said well-forming device to form an electrophoresis gel slab between said supporting plates, said gel slab having a plurality of sample wells along said side edge of said gel slab, each of said sample wells being formed at an angle with respect to a longitudinal dimension of said side edge of said gel slab for retaining a liquid sample when said side edge of said gel slab is oriented vertically.

18. The method of claim 17, comprising withdrawing said device from said gel slab by pulling said device in a linear direction with respect to a longitudinal dimension of said projections.

19. The method of claim 17, wherein said projections extend from said longitudinal edge of said well-forming device at an angle of about 30° to about 50° with respect to said longitudinal dimension of said device.

20. The method of claim 17, wherein said projections extend from said longitudinal edge at an angle of about 40° with respect to said longitudinal dimension of said device.

21. The method of claim 17, wherein each of said projections has a first side edge and a second side edge converging at an angle of about 5° to about 15° with respect to each other to a semicircular tip.

22. The method of claim 21, wherein adjacent projections define a substantially V-shaped recess therebetween, said recess having a curved bottom end.

23. The method of claim 17, wherein each of said projections has an axial passage extending therethrough and a removable pin received in said axial passage, said method comprising removing said pin after solidifying said gel-forming substance, and thereafter removing said well-forming device from said gel slab whereby air is drawn through said axial passage during removal to prevent distortion of said gel slab around said projections and to prevent collapse of said sample wells.

24. The method of claim 23, wherein said projections have a substantially circular cross-section and a rounded tip.

25. A process for separating substances by gel electrophoresis, said process comprising the steps of forming an electrophoresis gel slab having a first longitudinal edge and a plurality of spaced-apart sample wells along said longitudinal edge of said gel, said wells having an axial dimension defining a depth, said axial dimension of said wells being oriented at an incline with respect to said longitudinal edge of said gel slab, said gel slab further having a second longitudinal edge, placing a test liquid sample in each of said sample wells, positioning said gel slab in an electrophoresis tank with said longitudinal edge of said gel slab oriented vertically and said sample wells being positioned in said gel slab at an incline with respect to said longitudinal edge to retain said liquid samples in said wells, and contacting first and second longitudinal edges of said gel slab with a buffer solution and applying an electric potential between said first and second longitudinal ends of said gel slab to cause molecules in said samples to migrate through said gel slab.

26. The process of claim 25, wherein said electrophoresis gel slab is formed by providing a gel-forming substance between two spaced apart supporting plates having an open side edge;

positioning a well-forming device for forming sample wells in said open side edge of said supporting plates and into said gel-forming substance, said device having a body with a longitudinal edge with a longitudinal dimension, and a plurality of uniformly spaced apart projections extending from said body at an incline with respect to said longitudinal dimension; and solidifying said gel-forming substance to form an electrophoresis gel slab having a side edge and removing said well-forming forming device to form an electrophoresis gel slab between said supporting plates, said gel slab having a plurality of sample wells along said side edge of said gel slab, each of said sample wells being formed at an angle with respect to a longitudinal dimension of said side edge of said gel slab for retaining a liquid sample when said side edge of said gel slab is oriented vertically.

27. The process of claim 26, wherein said projections extend from said longitudinal edge of said well-forming device at an angle of about 30° to about 50° with respect to said longitudinal dimension.

28. The process of claim 26, wherein said projections extend from said longitudinal edge at an angle of about 40° with respect to said longitudinal dimension.

29. The process of claim 26, wherein said projections extend from said longitudinal edge at an angle of about 40° with respect to said longitudinal dimension.

30. The process of claim 29, wherein adjacent projections define a substantially V-shaped recess therebetween, said trough having a curved bottom end.

31. The process of claim 26, wherein each of said projections has an axial passage extending therethrough and a removable pin received in said axial passage, said method comprising removing said pin after solidifying said gel-forming substance, and thereafter removing said well-forming device from said gel slab whereby air is drawn through said axial passage during removal to prevent distortion of said gel slab around said projections and to prevent collapse of said sample wells.

32. The process of claim 31, wherein said projections have a substantially circular cross-section and a rounded tip.

33. The process of claim 25, comprising the steps of
providing a sample well forming member having a first side edge and a second side edge and having a plurality of parallel spaced apart channels extending between said first side edge and said second side edge and being oriented at an incline with respect to said first side edge, and
coupling said first side edge of said well forming member to said longitudinal edge of said gel slab wherein said channels form said sample wells and wherein said sample wells are in communication with said gel slab.

34. An assembly for forming a plurality of sample wells in an electrophoresis gel slab, said assembly comprising:
an electrophoresis gel slab having a longitudinal side edge;
a well-forming device having a body with a longitudinal edge and a longitudinal dimension; and
a plurality of spaced-apart projections extending from said longitudinal edge of said body at an incline with respect to said longitudinal dimension, said projections being oriented in a row and extending substantially parallel to each other, and said projections extending into said longitudinal edge of said gel slab and having a dimension to form a sample well in an edge of an electrophoresis gel slab, said projections being removable from said electrophoresis gel slab to form said sample wells.

35. The assembly of claim 34, wherein each of said projections extends from said longitudinal edge at an angle of about 30° to about 50° with respect to said longitudinal dimension.

36. The assembly of claim 34, wherein each of said projections has a substantially planar configuration with substantially parallel first and second side faces.

37. The assembly of claim 36, wherein each of said projections has a first side edge and second side edge extending between said first and second side faces, said first side edge extending from said longitudinal edge at a first angle and said second side edge extending from said longitudinal edge at a second angle whereby said first and second side edges converge toward an outer edge of said projection.

38. A method of forming an electrophoresis gel slab having a plurality of liquid sample wells, said method comprising the steps of:
positioning a well-forming device for forming sample wells in an open side edge of two spaced apart supporting plates and into a gel supported between said plates, said device having a body with a longitudinal edge with a longitudinal dimension, and a plurality of spaced-apart projections extending from said body at an incline with respect to said longitudinal dimension; and
removing said well-forming device to form an electrophoresis gel slab between said supporting plates, said gel slab having a plurality of sample wells along said side edge of said gel slab, each of said sample wells being formed at an angle with respect to a longitudinal dimension of said side edge of said gel slab for retaining a liquid sample when said side edge of said gel slab is oriented vertically.

39. The method of claim 38, comprising positioning said well-forming device in a gel-forming material, gelling said gel-forming material, and thereafter, removing said well-forming device from said gel.

40. The method of claim 38, wherein said projections extend from said longitudinal edge of said well-forming device at an angle of about 30° to about 50° with respect to said longitudinal dimension of said device.

41. The method of claim 38, wherein each of said projections has a first side edge and a second side edge converging at an angle of about 5° to about 15° with respect to each other to a semicircular tip.

42. The method of claim 41, wherein adjacent projections define a substantially V-shaped recess therebetween, said recess having a curved bottom end.

43. The method of claim 38, wherein said projections are uniformly spaced apart.

44. An electrophoresis gel having a substantially planar configuration with a longitudinal side edge, said longitudinal side edge having a plurality of sample receiving wells, each of said wells having an axial dimension defining a depth, said axial dimension of said wells being oriented at an incline with respect to said longitudinal edge to retain a liquid sample in said wells when said longitudinal side edge is oriented substantially vertical.

45. The electrophoresis gel of claim 44, further comprising a liquid sample in each of said wells.

46. The electrophoresis get of claim 44, wherein said electrophoresis gel is supported between two substantially parallel support plates.

47. The electrophoresis gel of claim 44, wherein said gel is produced by the process of:
positioning a well-forming device in an open side edge of an electrophoresis gel supported between two supporting plates to form said wells.

48. The electrophoresis gel of claim 47, wherein said well-forming device comprises a body having a longitudinal dimension and a longitudinal side edge, and a plurality of parallel projections extending from said longitudinal edge, said process comprising inserting said projections into said side edge of said gel to a depth to form said wells.

49. The electrophoresis gel of claim 48, wherein said projections extend from said longitudinal edge of said body at an incline with respect to said longitudinal dimension of said body.

50. The electrophoresis gel of claim 48, wherein said projections have a thickness less than a thickness of said gel.

51. The electrophoresis gel of claim 48, wherein said projections have substantially flat outer faces, and wherein said projections have a thickness substantially equal to a thickness of said gel.

52. The electrophoresis gel of claim 44, produced by the process of positioning a well-forming device in an open side of a gel-forming material supported between two support plates;
gelling said gel-forming material to form said electrophoresis gel; and
separating said well-forming device from said electrophoresis gel.

* * * * *

UNITED STATES PATENT AND TRADEMARK OFFICE
CERTIFICATE OF CORRECTION

PATENT NO. : 6,485,623 B1
DATED : November 26, 2002
INVENTOR(S) : Anderson It is certified that error appears in the above-identified patent and that said Letters Patent is hereby corrected as shown below:

<u>Column 1,</u>
Line 13, insert
-- This invention was made with United States Government Support under cooperative agreement number 70NANB5H1075 awarded by the National Institutes of Standards and Technolgy. --.

Signed and Sealed this

Sixth Day of September, 2005

JON W. DUDAS
*Director of the United States Patent and Trademark Office*